United States Patent [19]

Scheuffgen

[11] 4,401,664
[45] Aug. 30, 1983

[54] CREAM BASE COMPOSITION

[75] Inventor: Ingeborg Scheuffgen, Neuss, Fed. Rep. of Germany

[73] Assignee: Henkel Kommanditgesellschaft auf Aktien, Düsseldorf-Holthausen, Fed. Rep. of Germany

[21] Appl. No.: 328,995

[22] Filed: Dec. 9, 1981

[30] Foreign Application Priority Data

Aug. 5, 1981 [DE] Fed. Rep. of Germany ....... 3131006

[51] Int. Cl.³ ............................................. A61K 47/00
[52] U.S. Cl. .................................... 424/365; 424/170
[58] Field of Search ................................ 424/365, 358

[56] References Cited

U.S. PATENT DOCUMENTS

| | | | |
|---|---|---|---|
| 2,819,199 | 1/1958 | Kalish | 424/170 |
| 4,097,403 | 6/1978 | Tsutsumi et al. | 424/170 |
| 4,115,314 | 9/1978 | Oppenlaender et al. | 424/170 |
| 4,164,564 | 8/1979 | Chen | 424/170 |
| 4,254,104 | 3/1981 | Iazudi | 424/170 |
| 4,254,105 | 3/1981 | Fukuda | 424/170 |

FOREIGN PATENT DOCUMENTS

| | | | |
|---|---|---|---|
| 55-306 | 5/1981 | Japan | 424/361 |
| 2040680A | 9/1980 | United Kingdom | 424/362 |

*Primary Examiner*—Dale R. Ore
*Attorney, Agent, or Firm*—Hammond & Littell, Weissenberger and Muserlian

[57] ABSTRACT

This invention relates to a cream base composition. More particularly, this invention relates to a cream base composition consisting essentially of:
(a) about 70% by weight of glycerin mono-distearate;
(b) about 10% by weight of cetyl/stearyl alcohol;
(c) about 10% by weight of cetyl palmitate; and
(d) about 10% by weight of $C_{12}$–$C_{18}$-triglycerin, based upon the total weight of the composition.

1 Claim, No Drawings

CREAM BASE COMPOSITION

FIELD OF THE INVENTION

This invention relates to a cream base composition. More particularly, this invention relates to a cream base composition consisting essentially of glycerin mono-distearate, cetyl/stearyl alcohol, cetyl palmitate, and $C_{12}$–$C_{18}$-triglyceride in a specific quantitative ratio.

BACKGROUND OF THE INVENTION

Although fatty alcohols, partial glycerides, or mixtures thereof have been primarily used in the production of cosmetic or pharmaceutical emulsions, these consistency-enhancing agents have not been entirely satisfactory. In emulsions based upon fatty alcohols, there is an excessive viscosity rise during storage, and the emulsions have a mostly non-homogeneous structure. Other disadvantages are that the emulsions turn white when rubbed on the skin and that they cause an unpleasant skin sensation.

With regard to emulsions based upon partial glycerides, a great viscosity drop during storage at room temperature has been noticed. In addition, it has been observed that a gel phase forms during preparation of the emulsions. Furthermore, relatively large amounts, from about 15 to 16% by weight, based upon the weight of the total preparation, were required. To avoid these disadvantages, emulsions formed from combinations of fatty alcohols and partial glycerides were explored. However, these emulsions did not exhibit fully satisfactory results either.

OBJECTS OF THE INVENTION

It is an object of the invention to provide a novel cream base composition.

It is also an object of the invention to provide a non-self-emulsifying cream base which does not turn white when rubbed on the skin and which does not cause an unpleasant sensation on the skin.

It is a further object of the invention to provide a cream base consisting essentially of:
(a) about 70% by weight of glycerin mono-distearate;
(b) about 10% by weight of cetyl/stearyl alcohol;
(c) about 10% by weight of cetyl palmitate; and
(d) about 10% by weight of $C_{12}$–$C_{18}$-triglyceride,
based upon the total weight of the composition.

These and other objects of the invention will become more apparent in the discussion below.

DETAILED DESCRIPTION OF THE INVENTION

It is possible to prepare a suitable cream base composition by combining various known consistency-enhancing agents in a particular quantitative ratio. According to the invention herein a cream base composition is provided which consists essentially of:

(a) about 70% by weight of glycerin mono-distearate;
(b) about 10% by weight of cetyl/stearyl alcohol;
(c) about 10% by weight of cetyl palmitate; and
(d) about 10% by weight of $C_{12}$–$C_{18}$ triglyceride,
based upon the total weight of the cream base composition.

It has been found that the quantitative ratio of the individual components in the cream base is of paramount importance. If one component is omitted or if the quantitative ratio is varied to an appreciable degree, such as greater than about 1%, there can be a lessening of the advantages represented by the invention and even a substantial deterioration of the product, as is shown in the examples below.

The cream base composition of the invention meets all requirements of a good cream base. It is particularly characterized by the following:
(a) good viscosity stability over a long period of time;
(b) smooth structure and shiny surface of emulsions;
(c) good distribution over the skin without whiting effect;
(d) good temperature stability; and
(e) advantages regarding storage and production by by a consistency-enhancing agent.

With regard to components (a) to (d), glycerin mono-distearate is a partial glyceride of stearic acid with a ratio of 1 mol of glycerin to about 1.1 to 1.8 mols of stearic acid. Cetyl/stearyl alcohol is a mixture of from about 30 to 70 parts of cetyl alcohol to from about 70 to 30 parts of stearyl alcohol. Cetyl palmitate is the ester of palmitic acid with cetyl alcohol. $C_{12}$–$C_{18}$-triglyceride is the triglyceride of a $C_{12}$–$C_{18}$-fatty acid.

The cream base according to the invention can be combined with one or more conventional emulsifiers, such as, fatty alcohol sulfate, fatty alcohol oxethylate, partial glyceride oxethylate, or fatty acid oxythylate. These emulsifiers, either alone or in combination thereof, have been tested with the cream base composition of the invention in creams and liquid emulsions, and the advantageous properties of the cream base compositions of the invention have not been adversely effected by the conventional emulsifiers selected.

The following example are intended to illustrate the invention and should not be construed as limiting the invention thereof.

EXAMPLES

Examples I to IX

To demonstrate the importance of the particular quantitative ratio of the cream base composition of the invention, several comparison compositions (Examples I to VIII) and a composition according to the invention (Example IX) were prepared. The quantitative ratios of the components for each composition are set forth in the following table:

TABLE 1

| Example No. | I* | II* | III* | IV* | V* | VI* | VII* | VIII* | IX |
|---|---|---|---|---|---|---|---|---|---|
| Component (% by weight) | | | | | | | | | |
| (a) Glycerin mono-distearate | 60 | 60 | 70 | 65 | 40 | 60 | 70 | 60 | 70 |
| (b) Cetyl palmitate | 10 | 15 | 10 | 20 | 20 | 20 | 15 | 15 | 10 |
| (c) Cetyl/stearyl alcohol | 20 | 15 | 20 | 15 | 20 | 20 | 15 | 10 | 10 |
| (d) $C_{12}$–$C_{18}$—Triglyceride | 10 | 10 | — | — | 20 | — | — | 15 | 10 |

*Comparison

The compositions of Examples I to IX were evaluated for consistency, structure, and stability and then tested with regard to viscosity characteristics. The results of the evaluation and testing are set forth in the following table:

TABLE 2

| Example No. | I* | II* | III* | IV* | V* | VI* | VII* | VIII* | IX |
|---|---|---|---|---|---|---|---|---|---|
| Consistency | mildly soft | soft | mildly soft | soft | mildly soft | mildly soft | soft | soft | soft |
| Structure | non-homogeneous | lightly non-homogeneous | greatly non-homogeneous | smooth | non-homogeneous | lightly non-homogeneous | smooth | lightly non-homogeneous | smooth |
| Stability | stable | stable | stable | stable | stable | stable | stable | stable | stable |
| Viscosity (mPas): | | | | | | | | | |
| After 1 day | 19,500 | 400 | 11,400 | 14,900 | separated | 2,600 | 28,300 | 6,200 | 6,200 |
| After 12 weeks | 187,500 | 112,500 | 212,000 | 200,000 | — | 250,000 | 68,750 | 11,200 | 8,700 |

*Comparison

The following examples are intended to illustrate possible formulations for creams or emulsions based upon the cream base composition of the invention. In each instance a conventional, known preparation would typically comprise a quantity of glycerin mono-distearate equal to and in place of the cream base composition of the invention.

Example X

Day Cream

| Component | Percent by Weight |
|---|---|
| Cream base according to invention | 14 |
| Cetyl/stearyl alcohol with about 12 mols of ethylene oxide | 1.5 |
| Cetyl/stearyl alcohol with about 20 mols of ethylene oxide | 1.5 |
| Di-n-butyl adipate | 6 |
| 2-Octyldecanol | 6 |
| Glycerin, 86% | 6 |
| Water | 65 |
| TOTAL | 100 |

Example XI

Nutrient Cream

| Component | Percent by Weight |
|---|---|
| Cream base according to invention | 16 |
| Cetyl/stearyl alcohol with about 12 mols of ethylene oxide | 1.5 |
| Cetyl/stearyl alcohol with about 20 mols of ethylene oxide | 1.5 |
| Myritol 318 (fatty acid-glycerin ester, available from Henkel KGaA) | 10 |
| Oleic acid decyl ester | 10 |
| Glycerin, 86% | 5 |
| Water | 56 |
| TOTAL | 100 |

Example XII

Skin Emulsion

| Component | Percent by Weight |
|---|---|
| Cream base according to invention | 8 |
| Cetyl/stearyl alcohol with about 12 mols of ethylene oxide | 3 |
| Cetiol SN (isononanoic acid ester of saturated $C_{16}$–$C_{18}$-fatty alcohols, available from Henkel KGaA) | 10 |
| Glycerin, 86% | 5 |
| Water | 74 |
| TOTAL | 100 |

Example XIII

Skin Emulsion

| Component | Percent by Weight |
|---|---|
| Cream base according to invention | 8 |
| Cetyl/stearyl alcohol with about 12 mols of ethylene oxide | 3 |
| 2-Octyldecanol | 4 |
| Myritol 318 (fatty acid-glycerin ester) | 8 |
| Glycerin, 86% | 5 |
| Water | 72 |
| TOTAL | 100 |

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A cream base composition consisting of:
   (a) about 70% by weight of glycerin mono-distearate,
   (b) about 10% by weight of cetyl/stearyl alcohol,
   (c) about 10% by weight of cetyl palmitate, and
   (d) about 10% by weight of the triglyceride of a $C_{12}$–$C_{18}$ fatty acid, based upon the total weight of the cream base composition.

* * * * *